United States Patent [19]

Gaertner et al.

[11] Patent Number: 4,910,016

[45] Date of Patent: Mar. 20, 1990

[54] BACILLUS THURINGIENSIS ISOLATE

[75] Inventors: Frank H. Gaertner; George G. Soares; Jewel Payne, all of San Diego, Calif.

[73] Assignee: Mycogen Corporation, San Diego, Calif.

[21] Appl. No.: 80,845

[22] Filed: Aug. 3, 1987

[51] Int. Cl.$^4$ .................... A01N 63/00; A01N 65/00; C12N 1/22

[52] U.S. Cl. .................... 424/93; 424/195.1; 424/DIG. 8; 435/252.5; 435/832

[58] Field of Search ............... 424/93, 195.1, DIG. 8; 435/252.5, 832

[56] References Cited

U.S. PATENT DOCUMENTS

| | | | |
|---|---|---|---|
| 4,713,241 | 12/1987 | Wakisaka et al. | 424/93 |
| 4,766,203 | 8/1988 | Krieg et al. | 530/370 |
| 4,797,276 | 1/1989 | Herrnstadt et al. | 424/84 |

FOREIGN PATENT DOCUMENTS 0202739  11/1986  European Pat. Off. .

OTHER PUBLICATIONS

Couch, T. L., (1980), "Mosquito Pathogenicity of *Bacillus thuringiensis* var. Israelensis, " Developments in Industrial Microbiology, 22:61-67.

Beegle, C. C., (1978), "Use of Entomogenous Bacteria in Agroecosystems," Developments in Industrial Microbiology, 20:97-104.

Krieg, et al., Z. ang Ent., (1983), 96-500-508, (With translation).

*Primary Examiner*—John W. Rollins
*Attorney, Agent, or Firm*—Roman Saliwanchik; David R. Saliwanchik

[57] ABSTRACT

The subject invention concerns a novel and useful insecticide with activity against insect pests of the order Coleoptera and the order Lepidoptera. Pests in the order Coleoptera do heavy damage to crops, e.g., corn. The insecticide of the subject invention is a novel *B. thuringiensis* microbe referred to as B.t. MT 104, or mutants thereof. The spores or crystals of this microbe are useful to control coleopteran and lepidopteran pests in various environments.

15 Claims, 2 Drawing Sheets

HD-1 MT104 B.t. s.d.

BACILLUS THURINGIENSIS ISOLATE

BACKGROUND OF THE INVENTION

*Bacillus thuringiensis* (Bt) produces an insect toxin designated as δ-endotoxin. It is synthesized by the Bt sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of Bt covers insect species within the order Lepidoptera, many of which are major pests in agriculture and forestry. The activity spectrum also includes the insect order Diptera, which includes mosquitoes and black flies. See Couch, T.L., (1980) "Mosquito Pathogenicity of *Bacillus thuringiensis* var. israelensis," Developments in Industrial Microbiology 22:61–76; Beegle, C.C., (1978) "Use of Entomogenous Bacteria in Agroecosystems," Developments in Industrial Microbiology 20:97–104. Krieg, et al., Z. ang. Ent.(1983) 96:500–508, describe a Bt isolate named *Bacillus thuringiensis* var. tenebrionis, which is reportedly active against two beetles in the order Coleoptera. These are Colorado potato beetle, *Leptinotarsa decemlineata*, and *Agelastica alni*.

In European Patent Application 0 202 739 there is disclosed a novel Bt isolate active against Coleoptera. It is known as *B. thuringiensis* var. san diego (B.t.s.d.).

In the order Lepidoptera there are pest species that, in the larval stage, feed on foilage of crop plants. The larvae of many of these species are readily controlled by spraying foliage with commercial B.t. insecticides based on lepidopteran-active strains of B.t., such as the HD-1 strain. Coleopteran-active strains, such as B.t s.d., can be used in a similar manner to control foliar-feeding beetles. The Colorado potato beetle (*Leptinotarsa decemlineata*), for example, is susceptible to the delta-endotoxin of B.t.s.d. and larvae are killed upon ingesting a sufficient dose of spore/crystal preparation on treated foliage.

There are many agricultural crops which are attacked by pest species from both the order Coleoptera (beetles) and the order Lepidoptera (caterpillars). One of the limitations of currently available B.t. insecticides is that they can control species from one order or the other but not both. Thus a B.t. insecticide that can control both types of pests on a given crop would be very beneficial. Several examples of insect control where such a product could be very useful are given below.

Stored grains or other stored products such as flour, nuts, dried fruit, cereals, and the like, are attacked by a broad range of insect species. Most of these are either beetles or moths belonging to the orders Coleoptera and Lepidoptera, respectively. B.t. has been shown to be active against many of the moths attacking stored products. However, a serious limitation to its widespread use in controlling these Lepidopteran pests has been the selectivity of standard commercial B.t. preparations, i.e., they kill only Lepidopteran species and do not affect the beetles that are often present at the same time. For example, it would be desirable to have a pesticide that would be effective against the Indian meal moth, *Plodia interpunctella*, and the Mediterranean flour moth, *Anagasta kulniella*, as well as the flour beetles, *Tribolium castaneum* and *Tribolium confusum*, and, thus simultaneously control two of the major stored product pests in milled grain products.

The Mexican bean beetle, *Epilachna varivestis*, is a major pest of beans in the U.S. and Mexico. The adults and larvae feed on the foliage of bush and pole beans as well as on soybeans. In soybeans there is a complex of lepidopteran pests that includes the velvetbean caterpillar, *Anticarsia gemmatalis*, and the soybean looper, *Pseudoplusia includens*. A product that could control the bean beetle as well as the caterpillars occurring on soybeans would represent a major improvement over conventional products.

A number of crops are attacked by flea beetles. These beetles belong to the family Chrysomelidae, the same family as the Colorado potato beetle, *Leptinotarsa decemlineata*. The adults can cause extensive damage by feeding on the foliage. In many of these crops, lepidopteran defoliators also occur. Specific examples include cabbage and tobacco. In cabbage and related crucifers there are flea beetle species in the genus Phyllotreta that are serious problems. At the same time there are several caterpillars that are the major pests in cabbage. These include the cabbage looper, *Trichoplusia ni;* the diamondback moth, *Plutella xylostella;* and the imported cabbage worm, *Pieris rapae*. A product that could control the lepidopteran pest complex as well as the flea beetle species would have an obvious advantage over a more restricted B.t. product. A similar situation occurs in tobacco, with certain Epitrix spp. of flea beetle and the tobacco hornworm, *Manduca sexta*.

The above clearly depicts the need for an insecticide which can be used to control both coleopteran and lepidopteran pests.

BRIEF SUMMARY OF THE INVENTION

The subject invention concerns a novel *Bacillus thuringiensis* (Bt) isolate which has activity against both coleopteran and lepidopteran pests. For example, the novel Bt isolate, known herein as *Bacillus thuringiensis* MT 104 (B.t. MT 104), has thus far been shown to be active against the Colorado potato beetle (*Leptinotarsa decemlineata*), and the moths *Trichoplusia ni* and *Heliothis virescens*, the latter two being in the order Lepidoptera. More extensive host range studies are in progress.

The subject invention also includes mutants of B.t. MT 104 which have substantially the same pesticidal properties as B.t. MT 104. Procedures for making mutants are well known in the microbiological art. Ultraviolet light and nitrosoguanidine are used extensively toward this end.

Further, the invention also includes the treatment of substantially intact B.t. MT 104 cells to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated B.t. MT 104 cell acts as a protective coating for the pesticidal toxin. The toxin becomes available to act as such upon ingestion by a target insect.

DETAILED DISCLOSURE OF THE INVENTION

The novel *Bacillus thuringiensis* isolate of the subject invention has the following characteristics:

Characteristics of B.t. MT 104

Colony morphology—Large colony, dull surface, typical B.t.
Vegetative cell morphology—typical B.t.
Culture methods—Typical for B.t.
Flagellar serotyping—MT 104 belongs to serovar 8a8b, morrisoni.
Inclusions—Sporulating cells produce two crystalline inclusions, one flat square wafer, and one bipyramid.
Alkali-soluble proteins—SDS polyacrylamide gels show a 65,000 dalton protein, and a 130,000 dalton protein.
Coleopteran toxin—Bioassay shows activity against Colorado potato beetle.
Lepidopteran toxin—B.t. MT 104 is active against *Trichoplusia ni* and *Heliothis virescens*.

A comparison of the characteristics of the well-known B.t. strains *B. thuringiensis* var. kurstaki (HD-1), *B. thuringiensis* var. san diego (B.t.s.d.) and *B. thuringiensis* MT 104 (B.t. MT 104) is shown in Table 1.

TABLE 1
Comparison of B.t. HD-1, B.t. MT 104, and B.t.s.d.

| | B.t. HD-1 | B.t. MT 104 | B.t.s.d. |
|---|---|---|---|
| Serovar | kurstaki | morrisoni | morrisoni |
| Type of inclusion | Bipyramid | Square wafer & bipyramid | Square wafer |
| Size of alkali-soluble proteins | 130,000 60,000 | 130,000 64,000 | 64,000 |
| Host Range | Lepidoptera | Lepidoptera & Coleoptera | Coleoptera |

Figure 1:
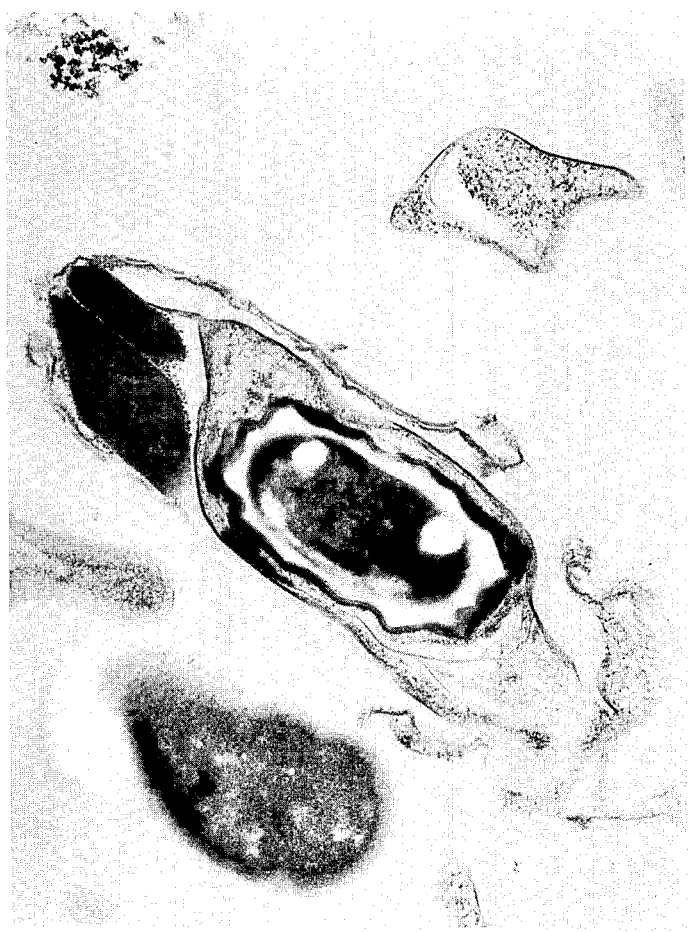
FIG. 1: An Electromicrograph Photograph of B.t. MT 104.
Figure 2:
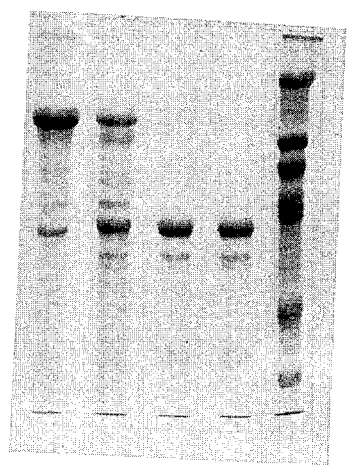
FIG. 2: A Photograph of a Standard SDS Polyacrylamide Gel of B.t. HD-1, B.T. MT 104, and B.t.s.d.

The culture disclosed in this application has been deposited in the Agricultural Research Service Patent Culture Collection (NRRL), Northern Regional Research Center, 1815 North University Street, Peoria, Illinois 61604, USA.

| Culture | Repository No. | Deposit Date |
|---|---|---|
| *Bacillus thuringiensis* MT 104 | NRRL B-18240 | July 17, 1987 |

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

B.t. MT 104, NRRL B-18240, can be cultured using standard art media and fermentation techniques. Upon completion of the fermentation cycle, the bacteria can be harvested by first separating the Bt spores and crystals from the fermentation broth by means well known in the art. The recovered Bt spores and crystals can be formulated into a wettable powder, liquid concentrate, granules or other formulations by the addition of surfactants, dispersants, inert carriers and other components to facilitate handling and application for particular target pests. These formulation and application procedures are all well known in the art and are used with commercial strains of *B. thuringiensis* (HD-1) active against Lepidoptera, e.g., caterpillars.

Formulated products can be sprayed or applied onto foilage to control phytophagous beetles or caterpillars.

Another approach that can be taken is to incorporate the spores and crystals of B.t. MT 104 into bait granules containing an attractant and applying these granules to the soil for control of soil-inhabiting Coleptera and Lepidoptera. Formulated B.t. MT 104 can also be applied as a seed-coating or root treatment or total plant treatment.

The B.t. MT 104 cells can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W.H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. MT 104, NRRL B-18240

A subculture of B.t. MT 104, NRRL B-18240 can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4$—$7H_2O$ | 2.46 g |
| $MnSO_4$—$H_2$ | 0.04 g |
| $ZnSO_4$—$7H_2O$ | 0.28 g |
| $FeSO_4$—$7H_2O$ | 0.40 g |
| $CaCl_2$ Solution (100 ml) | |
| $CaCl_2$—$2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The Bt spores and crystals, obtained in the above fermentation, can be isolated by procedures well known in the art. A frequently-used procedure is to subject the harvested fermentation broth to separation techniques, e.g., centrifugation.

EXAMPLE 2

Testing of B.t. MT 104, NRRL B-18240 Spores and Crystals

B.t. MT 104, NRRL B-18240 spores and crystals were tested against various insects. The insect species tested and a summary of the results are listed below in Table 2.

TABLE 2

| | Bioassay Results | |
|---|---|---|
| B.t. Isolate | $LC_{50}$ - T. ni | $LC_{50}$ - Colorado Potato Beetle |
| s.d. | no activity | 1.45 ml broth/100 ml |
| MT 104 | 0.80 µg tox/ml diet | 1.22 ml broth/100 ml |
| HD-1 | 0.302 µg tox/ml diet | no activity |

The assay for the Colorado potato beetle was conducted as follows:

B.t. spore/crystal preparations of varying concentrations were prepared. Potato leaves were dipped in these solutions, air dried, and exposed to 2nd instar Colorado potato beetle larvae. Each dosage was tested against 20 larvae and repeated 4 times. Mortality was determined after 96 hr. The LC-50 was determined by probit analysis. LC-50 refers to a lethal concentration that kills 50% of larvae.

The *T. ni* bioassay was performed using newly-hatched cabbage loopers. Various dilutions of the material being tested were mixed with an artificial insect diet and poured into small plastic trays. The larvae were placed on the diet mixture and allowed to feed for 6 days. The trays were then examined and the number of insects killed was recorded. The $LC_{50}$ was determined by probit analysis.

We claim:

1. A process for controlling insect pests belonging to the orders Coleoptera and Lepidoptera which comprises contacting said insect pests with an insect-controlling effective amount of *B. thuringiensis* MT 104, having the identifying characteristics of NRRL B-18240, or mutants thereof, which have substantially the same properties as *B. thuringiensis* Mt 104.

2. A process, according to claim 1, wherein said insect pests belong to the order Coleoptera.

3. A process, according to claim 1, wherein said insect pests belong to the order Lepidoptera.

4. A process, according to claim 1, wherein said insect pest is contacted with an insect-controlling effective amount of *B. thuringiensis* Mt 104, by incorporating said *B. thuringiensis* MT 104 into a bait granule and placing said granule on or in the soil when planting seed of a plant upon which plants said insect pests are known to feed.

5. A process for controlling soil-inhabiting insect pests of the order Coleoptera which comprises
  (1) preparing a bait granule comprising *B. thuringiensis* MT 104, or mutants thereof, which have substantially the same properties as *B. thuringiensis* Mt 104, spores or crystals; and
  (2) placing said bait granule on or in the soil.

6. A process, according to claim 5, wherein said bait granule is applied at the same time corn seed is planted in the soil.

7. A process, according to claims 1 or 5, wherein substantially intact B.t MT 104 cells, or mutants thereof, which have substantially the same properties as *B. thuringiensis* MT 104, are treated to prolong the pesticidal activity when the substantially intact cells are applied to the environment of a target pest.

8. A composition of matter comprising *B. thuringiensis* MT 104, or mutants thereof, which have substantially the same properties as *B. thuringiensis* MT 104, spores or crystals in association with an insecticide carrier.

9. A composition of matter, according to claim 8, wherein said carrier comprises beetle or caterpillar phagostimulants or attractants.

10. A composition of matter comprising *B. thuringiensis* MT 104, or mutants thereof, which have substantially the same properties as *B. thuringiensis* MT 104, in association with formulation ingredients applied as a seed coating.

11. *Bacillus thuringiensis* MT 104, having the identifying characteristics of NRRL B-18240, or mutants thereof, which have substantially the same properties as *B. thuringiensis* MT 104, having activity against insect pests of the order Coleoptera and the order Lepidoptera.

12. A process for simultaneously controlling insect pests from both the order Coleoptera and the order Lepidoptera which comprises contacting said insect pests with an insect-controlling effective amount of *B. thuringiensis* MT 104, having the identifying characteristics of NRRL B-18240, or mutants thereof, which have substantially the same properties as *B. thuringiensis* MT 104.

13. A process, according to claim 12, wherein the coleopteran and lepidopteran pests are present on stored products.

14. A process, according to claim 13, wherein the coleopteran pest is the Colorado potato beetle.

15. A process, according to claim 13, wherein the lepidopteran pest is *Trichoplusia ni* or *Heliothis virescens*.

* * * * *

UNITED STATES PATENT AND TRADEMARK OFFICE
CERTIFICATE OF CORRECTION

PATENT NO. : 4,910,016
DATED : March 20, 1990
INVENTOR(S) : Frank H. Gaertner, George G. Soares, Jewel Payne It is certified that error appears in the above-identified patent and that said Letters Patent is hereby corrected as shown below:

Column 6:     line 14:     "Mt 104" should read --MT 104--.
                 line 22:     "Mt" should read --MT--.

Signed and Sealed this

Eighth Day of October, 1991

Attest:

HARRY F. MANBECK, JR.

*Attesting Officer*        *Commissioner of Patents and Trademarks*